US00PP31181P2

(12) United States Plant Patent
Heuger

(10) Patent No.: US PP31,181 P2
(45) Date of Patent: Dec. 3, 2019

(54) ***HELLEBORUS* PLANT NAMED 'COSEH 4700'**

(50) Latin Name: ***Helleborus* x *ericsmithii* X *Helleborus* x *hybridus***
Varietal Denomination: COSEH 4700

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/350,426

(22) Filed: Nov. 15, 2018

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 6/72
See application file for complete search history.

(56) References Cited

PUBLICATIONS

PLUTO Plant Variety Database Jun. 19, 2019. p. 1.*

* cited by examiner

*Primary Examiner* — Annette H Para
(74) *Attorney, Agent, or Firm* — C. A. Whealy

(57) ABSTRACT

A new and distinct cultivar of *Helleborus* plant named 'COSEH 4700', characterized by its relatively tall, upright and mounded plant habit; moderately vigorous to vigorous growth habit; dark green-colored leaves; moderately freely flowering habit; single dark greyed purple-colored flowers; and good garden performance.

2 Drawing Sheets

Botanical designation: *Helleborus* x *ericsmithii* X *Helleborus* x *hybridus*.

Cultivar denomination: 'COSEH 4700'.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 4700'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in February, 2013 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in 2014.

Asexual reproduction of the new *Helleborus* plant by divisions in a controlled environment in Glandorf, Germany since 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 4700'. These characteristics in combination distinguish 'COSEH 4700' as a new and distinct *Helleborus* plant:

1. Relatively tall, upright and mounded plant habit.
2. Moderately vigorous to vigorous growth habit.
3. Dark green-colored leaves.
4. Moderately freely flowering habit.
5. Single dark greyed purple-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have dark greyed purple-colored flowers whereas plants of the female parent selection have cream to pink-colored flowers.

Plants of the new *Helleborus* differ from plants of the male parent selection in the following characteristics:

1. Plants of the new *Helleborus* are taller than plants of the male parent selection.
2. Plants of the new *Helleborus* have dark greyed purple-colored flowers whereas plants of the male parent selection have red-colored flowers.

Plants of the new *Helleborus* can be compared to plants of *Helleborus* x *hybridus* 'Annas Red', not patented. In side-by-side comparisons, plants of the new *Helleborus* differ primarily from plants of 'Annas Red' in leaf venation as plants of the new *Helleborus* have less distinct leaf venation than plants of 'Annas Red'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 4700' grown in a container.

The photograph on the second sheet is a close-up view of a typical flower of 'COSEH 4700'.

DETAILED BOTANICAL DESCRIPTION

The aforementioned photographs and following observations, measurements and values describe plants grown during November in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 16 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 4700'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro meristem culture.

*Time to initiate roots, winter*.—About 50 days at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Moderately branching; sparse.

Plant description:

*Plant and growth habit*.—Herbaceous perennial; relatively tall, upright and mounding plant habit with flowers held within and above the foliar plane; plant shape, roughly flattened globular; moderately vigorous to vigorous growth habit; moderate growth rate.

*Plant height, soil level to top of foliar plane*.—About 30.4 cm.

*Plant height, soil level to top of flowers*.—About 35.7 cm.

*Plant diameter* (*area of spread*).—About 55 cm.

Leaf description:

*Arrangement*.—Leaves arranged in a basal rosette; leaves palmately compound with typically five leaflets per leaf.

*Leaf length*.—About 25.5 cm.

*Leaf width*.—About 28.6 cm.

*Leaflet length*.—About 16.5 cm.

*Leaflet width*.—About 8 cm.

*Leaf shape*.—Palmate; reniform in outline.

*Leaflet shape*.—Ovate to elliptic.

*Leaflet apex*.—Acute to apiculate.

*Leaflet base*.—Attenuate.

*Leaflet margin*.—Coarsely serrate; slightly undulate.

*Leaflet texture and luster, upper and lower surfaces*.—Smooth, glabrous; leathery; slightly glossy.

*Leaflet venation pattern*.—Pinnate.

*Leaflet color*.—Developing leaflets, upper surface: Close to NN137A; midvein, close to 187A. Developing leaflets, lower surface: Close to N186C; midvein, close to between N186C and N200A. Fully developed leaflets, upper surface: Close to darker than between 139A and N189A; venation, close to 146B. Fully developed leaflets, lower surface: Close to between 147B and 191A; venation, close to between N186C and 187A.

*Petioles*.—Length: About 20.7 cm. Diameter: About 6 mm to 8 mm. Strength: Strong. Texture and luster, upper and lower surfaces: Smooth, glabrous; moderately glossy. Color, upper and lower surfaces: Close to N186C; densely covered with small dots, close to 146A.

Flower description:

*Flower shape and habit*.—Single rotate flowers; arranged solitary or in clusters with about seven flowers each; moderately freely flowering habit with about 26 flowers developing per plant; flowers facing outwardly to nodding.

*Fragrance*.—None detected.

*Natural flowering season*.—Plants begin flowering about ten months after planting; plants flower during the late autumn into the winter in Germany.

*Flower longevity on the plant*.—About ten days; sepals persistent, other flower parts are not persistent.

*Flower buds*.—Length: About 2.4 cm. Diameter: About 1.4 cm. Shape: Broadly ovoid. Texture and luster: Smooth, glabrous; slightly glossy. Color: Close to 59A and N186C.

*Inflorescence height*.—About 36.3 cm.

*Inflorescence diameter*.—About 15.8 cm.

*Flower diameter*.—About 10.4 cm.

*Flower depth* (*height*).—About 4 cm.

*Petals*.—Transformed into nectaries.

*Sepals*.—Quantity and arrangement: About five, arranged in a single whorl. Length: About 5.2 cm. Width: About 4.6 cm. Shape: Broadly ovate to broadly elliptic, slightly concave. Apex: Obtuse. Base: Cuneate. Margin: Entire; slightly to moderately undulate. Texture and luster, upper surface: Smooth, glabrous; matte. Texture and luster, lower surface: Smooth, glabrous; slightly glossy. Color: When opening, upper surface: Close to between 59D to 60C; fine dots, close to N186C. When opening, lower surface: Close to 59B; fine dots, close to 187A; venation, close to N186C. Fully opened, upper surface: Close to 187B; fine dots, close to N186C. Fully opened, lower surface: Close to 187B; venation, close to N186C.

*Flower bracts*.—Quantity per flower: Typically two. Length: About 12.2 cm. Width: About 7.4 cm. Shape: Obovate to tri-lobed. Apex: Acute. Base: Cuneate. Margin: Serrate; moderately undulate. Color, upper surface: Close to between NN137A and 147A. Color, lower surface: Close to N186C.

*Peduncles*.—Length: About 28.4 cm. Diameter: About 1 cm to 1.1 cm. Aspect: About 10° from vertical. Strength: Strong. Texture and luster: Smooth, glabrous; moderately glossy. Color: Close to 187B; flushed with close to 148D; fine dots, close to 148D.

*Pedicels*.—Length: About 4.5 cm. Diameter: About 2.5 mm to 3 mm. Aspect: About 20° from peduncle axis. Strength: Moderately strong. Texture and luster: Smooth, glabrous; moderately glossy. Color: Close to N186C.

*Reproductive organs*.—Stamens: Quantity per flower: About 120. Filament length: About 1.7 cm. Filament color: Close to 150D fading proximally to closer to 186D. Anther shape: Reniform; basifixed. Anther size: About 2 mm by 3 mm. Anther color: Close to 1D. Pollen amount: Scarce. Pollen color: Close to 4D. Pistils: Quantity per flower: About three to six. Pistil length: About 1.5 cm. Stigma diameter: About 0.3 mm. Stigma shape: Club-shaped. Stigma color: Close to 157D. Style length: About 1.45 cm. Style color: Close to N186C. Ovary color: Close to 184B; stripes, close to 183A. Nectaries (transformed petals): Quantity per flower: About. 13. Length: About 1.2 cm. Diameter: About 7 mm. Shape: Tubular, flattened. Texture and luster, inner and outer surfaces: Smooth, glabrous; matte. Color, immature, inner and outer surfaces: Close to N144D. Color, mature, inner and outer surfaces: Close to N144D; distally, close to 151C; distal color becoming closer to 2A with development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 4700' as illustrated and described.

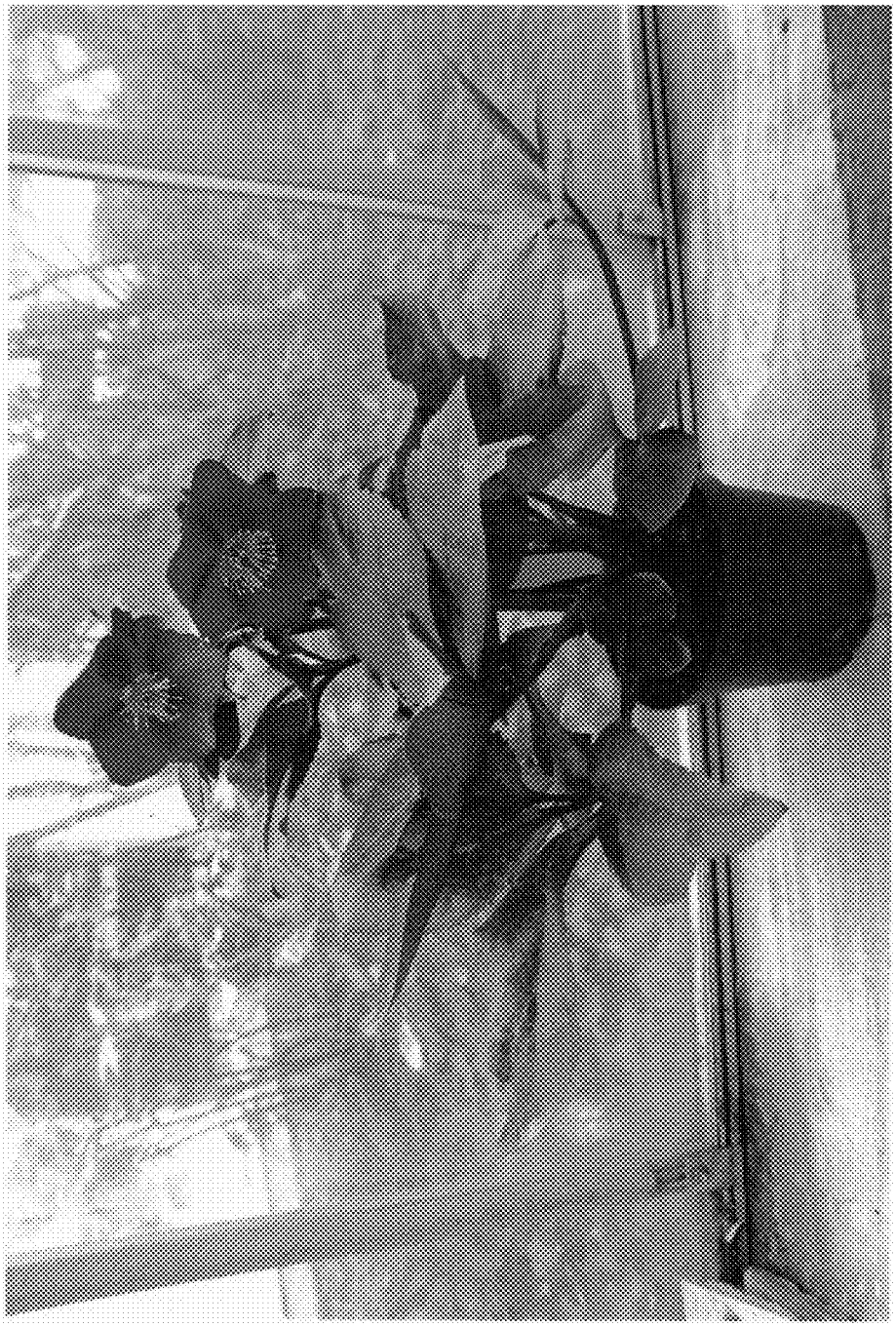

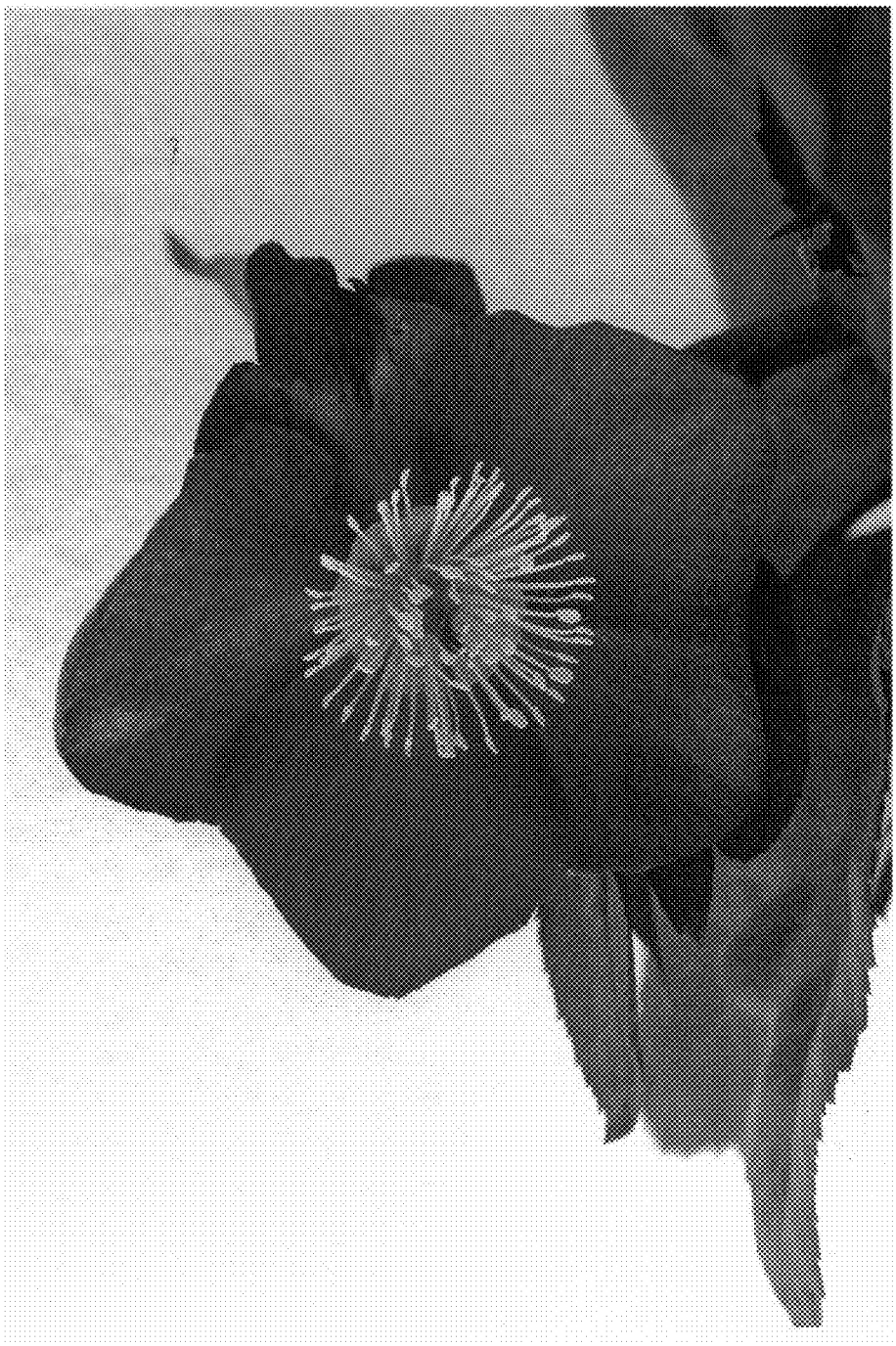

* * * * *